United States Patent
Schuessler et al.

(10) Patent No.: US 8,551,060 B2
(45) Date of Patent: *Oct. 8, 2013

(54) SUBATMOSPHERIC PRESSURE MECHANISM FOR WOUND THERAPY SYSTEM AND RELATED METHODS THEREFOR

(75) Inventors: Wayne Schuessler, St. Louis, MO (US); Ricky A. Sisk, Washington, MO (US)

(73) Assignee: Smith & Nephew, Inc., Andover, MA (US)

( * ) Notice: Subject to any disclaimer, the term of this patent is extended or adjusted under 35 U.S.C. 154(b) by 89 days.

This patent is subject to a terminal disclaimer.

(21) Appl. No.: 13/186,599

(22) Filed: Jul. 20, 2011

(65) Prior Publication Data

US 2011/0276017 A1   Nov. 10, 2011

Related U.S. Application Data

(63) Continuation of application No. 12/175,038, filed on Jul. 17, 2008, now Pat. No. 8,007,481.

(51) Int. Cl.
*A61M 1/00* (2006.01)

(52) U.S. Cl.
USPC ........... 604/313; 604/187; 604/192; 604/268; 604/289; 604/296; 604/300; 604/311; 604/312; 604/315; 604/316; 604/119

(58) Field of Classification Search
USPC .................... 604/311, 312, 313, 315, 316
See application file for complete search history.

(56) References Cited

U.S. PATENT DOCUMENTS

| | | |
|---|---|---|
| 3,367,332 A | 2/1968 | Groves |
| 3,486,504 A | 12/1969 | Austin, Jr. |
| 3,572,340 A | 3/1971 | Lloyd et al. |
| 3,712,298 A | 1/1973 | Snowdon et al. |
| 3,809,086 A | 5/1974 | Schachet et al. |

(Continued)

FOREIGN PATENT DOCUMENTS

| | | |
|---|---|---|
| DE | 41 11 122 A1 | 4/1993 |
| DE | 295 04 378 | 10/1995 |

(Continued)

OTHER PUBLICATIONS

Meyer, M.D., et al, "In Surgery, Medicine and the Specialties a Manual of its Practical Application", Bier's Hyperemic Treatment, Second Revised Edition, W.B. Saunders Company, 1909.

(Continued)

*Primary Examiner* — Tatyana Zalukaeva
*Assistant Examiner* — Ilya Treyger
(74) *Attorney, Agent, or Firm* — Knobbe, Martens, Olson & Bear, LLP

(57) ABSTRACT

A portable system for subatmospheric pressure therapy in connection with healing a surgical wound is provided. The system includes a wound dressing dimensioned for positioning relative to a wound bed of a subject, and a collection canister in fluid communication with the wound dressing. The canister includes a base defining a fluid receiving cavity and having a fluid inlet port and a vacuum port. The fluid inlet port is configured for fluid communication with a wound dressing, The system further includes a cover selectively engageable to the base, e.g., in a snap-fit manner. The cover is configured to receive a control unit and has a vent assembly for exhausting the control unit. A seal member is interposed relative to the base and the cover to establish and maintain a substantial sealed relationship between the two components when assembled.

20 Claims, 6 Drawing Sheets

(56) References Cited

U.S. PATENT DOCUMENTS

| | | |
|---|---|---|
| 3,874,387 A | 4/1975 | Barbieri |
| 4,080,970 A | 3/1978 | Miller |
| 4,112,947 A | 9/1978 | Nehring |
| 4,112,949 A | 9/1978 | Rosenthal et al. |
| 4,136,696 A | 1/1979 | Nehring |
| 4,266,545 A | 5/1981 | Moss |
| 4,382,441 A | 5/1983 | Svedman |
| 4,524,064 A | 6/1985 | Nambu |
| 4,743,232 A | 5/1988 | Kruger |
| 4,969,880 A | 11/1990 | Zamierowski |
| 4,990,137 A | 2/1991 | Graham |
| 4,997,438 A | 3/1991 | Nipper |
| 5,071,409 A | 12/1991 | Rosenberg |
| 5,100,395 A | 3/1992 | Rosenberg |
| 5,100,396 A | 3/1992 | Zamierowski |
| 5,106,629 A | 4/1992 | Cartmell et al. |
| 5,141,503 A | 8/1992 | Sewell, Jr. |
| 5,149,331 A | 9/1992 | Ferdman et al. |
| 5,152,757 A | 10/1992 | Eriksson |
| 5,160,322 A | 11/1992 | Scheremet et al. |
| 5,176,663 A | 1/1993 | Svedman et al. |
| 5,178,157 A | 1/1993 | Fanlo |
| 5,195,977 A | 3/1993 | Pollitt |
| 5,261,893 A | 11/1993 | Zamierowski |
| 5,263,922 A | 11/1993 | Sova et al. |
| D364,679 S | 11/1995 | Heaton et al. |
| 5,484,427 A | 1/1996 | Gibbons |
| 5,527,293 A | 6/1996 | Zamierowski |
| 5,536,233 A | 7/1996 | Khouri |
| 5,549,584 A | 8/1996 | Gross |
| 5,588,958 A | 12/1996 | Cunningham et al. |
| 5,636,643 A | 6/1997 | Argenta et al. |
| 5,645,081 A | 7/1997 | Argenta et al. |
| 5,678,564 A | 10/1997 | Lawrence et al. |
| 5,701,917 A | 12/1997 | Khouri |
| 5,733,305 A | 3/1998 | Fleischmann |
| 5,840,049 A | 11/1998 | Tumey et al. |
| 5,911,222 A | 6/1999 | Lawrence et al. |
| 5,944,703 A | 8/1999 | Dixon et al. |
| 6,010,524 A | 1/2000 | Fleischmann |
| 6,071,267 A | 6/2000 | Zamierowski |
| 6,117,111 A | 9/2000 | Fleischmann |
| 6,135,116 A | 10/2000 | Vogel et al. |
| D434,150 S | 11/2000 | Tumey et al. |
| 6,142,982 A | 11/2000 | Hunt et al. |
| 6,174,306 B1 | 1/2001 | Fleischmann |
| 6,203,563 B1 | 3/2001 | Fernandez |
| 6,261,276 B1 | 7/2001 | Reitsma |
| 6,325,788 B1 | 12/2001 | McKay |
| 6,345,623 B1 | 2/2002 | Heaton et al. |
| 6,348,423 B1 | 2/2002 | Griffiths et al. |
| 6,398,767 B1 | 6/2002 | Fleischmann |
| 6,406,447 B1 | 6/2002 | Thrash et al. |
| 6,420,622 B1 | 7/2002 | Johnston et al. |
| 6,458,109 B1 | 10/2002 | Henley et al. |
| 6,488,643 B1 | 12/2002 | Tumey et al. |
| 6,500,112 B1 | 12/2002 | Khouri |
| D469,175 S | 1/2003 | Hall et al. |
| D469,176 S | 1/2003 | Hall et al. |
| 6,520,982 B1 | 2/2003 | Boynton et al. |
| 6,553,998 B2 | 4/2003 | Heaton et al. |
| D475,134 S | 5/2003 | Randolph |
| 6,557,704 B1 | 5/2003 | Randolph |
| D478,659 S | 8/2003 | Hall et al. |
| 6,607,495 B1 | 8/2003 | Skalak et al. |
| 6,626,891 B2 | 9/2003 | Ohmstede |
| 6,648,862 B2 | 11/2003 | Watson |
| 6,685,681 B2 | 2/2004 | Lockwood et al. |
| 6,695,823 B1 | 2/2004 | Lina et al. |
| 6,695,824 B2 | 2/2004 | Howard et al. |
| D488,558 S | 4/2004 | Hall |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,887,228 B2 | 5/2005 | McKay |
| 6,887,263 B2 | 5/2005 | Bleam et al. |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 6,960,181 B2 | 11/2005 | Stevens |
| 6,979,324 B2 | 12/2005 | Bybordi et al. |
| 6,994,702 B1 | 2/2006 | Johnson |
| 7,022,113 B2 | 4/2006 | Lockwood et al. |
| 7,037,254 B2 | 5/2006 | O'Connor et al. |
| 7,052,167 B2 | 5/2006 | Vanderschuit |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,128,719 B2 | 10/2006 | Rosenberg |
| 7,128,735 B2 | 10/2006 | Weston |
| 7,144,390 B1 | 12/2006 | Hannigan et al. |
| 7,169,151 B1 | 1/2007 | Lytinas |
| 7,182,758 B2 | 2/2007 | McCraw |
| 7,195,624 B2 | 3/2007 | Lockwood et al. |
| 7,198,046 B1 | 4/2007 | Argenta et al. |
| 7,214,202 B1 | 5/2007 | Vogel et al. |
| 7,216,651 B2 | 5/2007 | Argenta et al. |
| D544,092 S | 6/2007 | Lewis |
| 7,273,054 B2 | 9/2007 | Heaton et al. |
| 7,276,051 B1 | 10/2007 | Henley et al. |
| 7,279,612 B1 | 10/2007 | Heaton et al. |
| 7,316,672 B1 | 1/2008 | Hunt et al. |
| D565,177 S | 3/2008 | Locke et al. |
| 7,338,482 B2 | 3/2008 | Lockwood et al. |
| 7,351,250 B2 | 4/2008 | Zamierowski |
| 7,361,184 B2 | 4/2008 | Joshi |
| 7,381,211 B2 | 6/2008 | Zamierowski |
| 7,381,859 B2 | 6/2008 | Hunt et al. |
| 7,396,345 B2 | 7/2008 | Knighton et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 7,731,702 B2 | 6/2010 | Bybordi et al. |
| 2001/0031943 A1 | 10/2001 | Urie |
| 2001/0043943 A1 | 11/2001 | Coffey |
| 2002/0016577 A1 | 2/2002 | Ohmstede |
| 2002/0143286 A1 | 10/2002 | Tumey |
| 2002/0151836 A1 | 10/2002 | Burden |
| 2003/0093041 A1 | 5/2003 | Risk, Jr. et al. |
| 2003/0208149 A1 | 11/2003 | Coffey |
| 2003/0212357 A1 | 11/2003 | Pace |
| 2003/0212359 A1 | 11/2003 | Butler |
| 2003/0219469 A1 | 11/2003 | Johnson et al. |
| 2004/0006319 A1 | 1/2004 | Lina et al. |
| 2004/0030304 A1 | 2/2004 | Hunt et al. |
| 2004/0039415 A1 | 2/2004 | Zamierowski |
| 2004/0064132 A1 | 4/2004 | Boehringer et al. |
| 2004/0073151 A1 | 4/2004 | Weston |
| 2004/0093026 A1 | 5/2004 | Weidenhagen et al. |
| 2004/0122434 A1 | 6/2004 | Argenta et al. |
| 2004/0193218 A1 | 9/2004 | Butler |
| 2004/0241213 A1 | 12/2004 | Bray |
| 2004/0243073 A1 | 12/2004 | Lockwood et al. |
| 2005/0010153 A1 | 1/2005 | Lockwood et al. |
| 2005/0020955 A1 | 1/2005 | Sanders et al. |
| 2005/0070835 A1 | 3/2005 | Joshi |
| 2005/0070858 A1 | 3/2005 | Lockwood et al. |
| 2005/0085795 A1 | 4/2005 | Lockwood et al. |
| 2005/0177190 A1 | 8/2005 | Zamierowski |
| 2005/0182445 A1 | 8/2005 | Zamierowski |
| 2005/0222527 A1 | 10/2005 | Miller et al. |
| 2005/0222544 A1 | 10/2005 | Weston |
| 2005/0261642 A1 | 11/2005 | Weston |
| 2005/0261643 A1 | 11/2005 | Bybordi et al. |
| 2006/0015087 A1 | 1/2006 | Risk, Jr. et al. |

| | | | |
|---|---|---|---|
| 2006/0025727 | A1 | 2/2006 | Boehringer et al. |
| 2006/0039742 | A1 | 2/2006 | Cable, Jr. et al. |
| 2006/0041247 | A1 | 2/2006 | Petrosenko et al. |
| 2006/0079852 | A1 | 4/2006 | Bubb et al. |
| 2006/0100586 | A1 | 5/2006 | Karpowicz et al. |
| 2006/0100594 | A1 | 5/2006 | Adams et al. |
| 2006/0116620 | A1 | 6/2006 | Oyaski |
| 2007/0014837 | A1 | 1/2007 | Johnson et al. |
| 2007/0016152 | A1 | 1/2007 | Karpowicz et al. |
| 2007/0021697 | A1 | 1/2007 | Ginther et al. |
| 2007/0027414 | A1 | 2/2007 | Hoffman et al. |
| 2007/0032754 | A1 | 2/2007 | Walsh |
| 2007/0032755 | A1 | 2/2007 | Walsh |
| 2007/0032778 | A1 | 2/2007 | Heaton et al. |
| 2007/0055209 | A1 | 3/2007 | Patel et al. |
| 2007/0066946 | A1 | 3/2007 | Haggstrom et al. |
| 2007/0078366 | A1 | 4/2007 | Haggstrom et al. |

FOREIGN PATENT DOCUMENTS

| | | |
|---|---|---|
| DE | 43 06 478 | 12/2008 |
| EP | 0 020 662 | 7/1984 |
| EP | 0358302 | 5/1989 |
| EP | 0 358 302 | 3/1990 |
| EP | 0 853 950 | 10/2002 |
| GB | 1 549 756 | 3/1977 |
| GB | 2 195 255 | 4/1988 |
| GB | 2 235 877 | 3/1991 |
| SU | 1762940 | 1/1989 |
| WO | 80/01139 | 6/1980 |
| WO | 80/02182 | 10/1980 |
| WO | 84/01904 | 5/1984 |
| WO | 89/05133 | 6/1989 |
| WO | 90/11795 | 10/1991 |
| WO | 92/19313 | 11/1992 |
| WO | 96/05873 | 2/1996 |
| WO | 03057307 | 7/2003 |
| WO | 03101508 | 12/2003 |
| WO | 2005009488 | 2/2005 |

OTHER PUBLICATIONS

Jeter, Katherine F., et al., "Managing Draining Wounds and Fistulae: New and Established Methods", Chronic Wound Care, 1990, pp. 240-246.

Chariker, M. E. et al. (eds), "Effective Management of Incisional and Cutaneous Fistulae with Closed Suction Wound Drainage," Contemporary Surgery, vol. 34, Jun. 1989, pp. 59-63.

B.M. Kostiuchenok, et al., "The Vacuum Effect in the Surgical Treatment of Purulent Wounds," Russian Journal: Vestnik Khirurgii, Sep. 1986 (18-21).

Y.N. Usupov, et al., "Active Wound Drainage," Russian Journal: Vestnik Khirugii, Apr. 1987 (42-45).

Yu A. Davydov, et al., "Concepts for Clinical Biological Management of the Wound Process in the Treatment of Purulent Wounds Using Vacuum Therapy," Vestnik Khirugii, Feb. 1991, 132-135).

Gorica Zivadinovic, et al., "Vacuum Therapy in the Treatment of Peripheral Blood Vessels," Conference Papers of the 5th Timok Medical Days, Majdanpek, 1986 (161-164).

Ryosuke Fujimoro, M.D., et al., "Sponge Fixation Method for Treatment of Early Scars," From the Department of Dermatology in the Faculty Medicine, Kyoto University, vol. 42, No. 4, Oct. 1968 (323-326).

W. Fleischmann, et al., Vacuum Sealing: Indication, Technique and Results, Emr J Orthop Surg Tramatol (1995) 5:37-40.

Sherry Stoll, "Energetic Remedies—Cupping: Healing Within a Vacuum," https://www.suite101.com/article.cfm/energetic)remediesf74531, Apr. 13, 2005.

Mulder, G.D, et al., "Clinicians' Pocket Guide to Chronic Wound Repair," Wound Healing Publications Second Edition, 1991.

Yu A. Davydov, et al., "Vacuum Therapy in the Treatment of Purulent Lactation Mastitis," Russian Journal: Vesnik Khirurgii, Sep. 1986 (66-70).

Yu A. Davydov, et al., "Bacteriological and Cytological Assessment of Vacuum Therapy of Purulent Wounds", Vestnik Khirurgii, Oct. 1988 (48-52).

Göran Sanden, M.D., et al., "Staphylococcal Wound Infection in the Pig: Part II. Innoculation, Quantification of Bacteria, and Reproducibility," Annals of Plastic Surgery, vol. 23, No. 3, Sep. 1989, (219-223).

Björn, et al., "Irrigation Treatment in Split-thickness Skin Grafting of Intractable Leg Ulcers," Scand J Plast Reconstr Surg 19: 211-213, 1985.

Paul Svedman, et al., "Staphylococcal Wound Infection in the Pig: Part I. Course," Annals of Plastic Surgery, vol. 23, No. 3, Sep. 1989 (212-218).

Paul Svedman, "A Dressing Allowing Continuous Treatment of a Biosurface," IRCS Medical Science: Biomedical Technology; Clinical Medicine; Surgery and Transplantation, 7, 221 (1979).

Paul Svedman, "Irrigation Treatment of Leg Ulcers," The Lancet, Sep. 3, 1983 (532-534).

P. Svedman, "A Dressing System Providing Fluid Supply and Suction Drainage Used for Continuous or Intermittent Irrigation," Annals of Plastic Surgery, vol. 17, No. 2, Aug. 1986 (125-133).

Yu a. Davydov, et al., "Vacuum Therapy in treatment of Acute Purulent Diseases of Soft Tissues and Purulent Wounds," Vestnik Khirurgii, (Surgeon's Herald), Medicine Publishers, 1986.

US 6,216,701, 04/2001, Heaton et al. (withdrawn)

US 7,186,244, 03/2007, Hunt et al. (withdrawn)

SUBATMOSPHERIC PRESSURE MECHANISM FOR WOUND THERAPY SYSTEM AND RELATED METHODS THEREFOR

CROSS-REFERENCE TO RELATED APPLICATION

This application is a continuation application of and claims the benefit of priority under 35 U.S.C. §120 to co-pending U.S. patent application Ser. No. 12/175,038, titled SUBATMOSPHERIC PRESSURE MECHANISM FOR WOUND THERAPY SYSTEM, filed on Jul. 17, 2008, which is incorporated herein by reference in its entirety for all purposes.

BACKGROUND

1. Technical Field

The present disclosure relates to treating an open wound, and, more specifically, relates to a wound therapy system including an improved subatmospheric pressure mechanism.

2. Background of Related Art

Wound closure involves the migration of epithelial and subcutaneous tissue adjacent the wound towards the center and away from the base of the wound until the wound closes. Unfortunately, closure is difficult with large wounds, chronic wounds or wounds that have become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but, are also less able to successfully fight microbial infection and, thus, are less able to close the wound naturally. Such wounds have presented difficulties to medical personnel for many years.

Negative pressure therapy also known as suction or vacuum therapy has been used in treating and healing wounds. Application of negative pressure, e.g. reduced or subatmospheric pressure, to a localized reservoir over a wound has been found to assist in closing the wound by promoting blood flow to the area, stimulating the formation of granulation tissue, and encouraging the migration of healthy tissue over the wound. Negative pressure may also inhibit bacterial growth by drawing fluids from the wound such as exudates, which may tend to harbor bacteria. This technique has proven particularly effective for chronic or healing-resistant wounds, and is also used for other purposes such as post-operative wound care.

Generally, negative pressure therapy provides for a wound to be covered to facilitate suction at the wound area. A conduit is introduced through the wound covering to provide fluid communication to an external vacuum source. Atmospheric gas, wound exudates, or other fluids may thus be drawn from the wound area through the fluid conduit to stimulate healing of the wound. Exudates drawn from the wound area may be deposited in a collection canister or container.

Subatmospheric pressure mechanisms used in wound therapy systems may include a cavity or chamber for receiving the removed exudates, a vacuum source, and a power source. The pressure mechanisms are configured to provide the suction that draws exudates from the wound. Unfortunately, conventional subatmospheric pressure mechanisms have a tendency to develop leaks. Leaks may reduce the efficiency of the system and/or create odor and wetness issues.

SUMMARY

Accordingly, the present disclosure relates to an improved subatmospheric pressure mechanism. A portable system for subatmospheric pressure therapy in connection with healing a surgical wound is provided. The system includes a wound dressing dimensioned for positioning relative to a wound bed of a subject, and a collection canister in fluid communication with the wound dressing. The canister may include a base defining a fluid receiving cavity and having a fluid inlet port and a vacuum port. The fluid inlet port is configured for fluid communication with a wound dressing. A cover is selectively engageable to the base, e.g., in a snap-fit manner. The cover accommodates a control unit and a vent assembly for exhausting the control unit. A seal member is interposed relative to the base and the cover and is adapted to establish and maintain a sealed relationship between these components. At least one of the fluid inlet port and the vacuum port may be configured to receive a cap.

The control unit of the system may include a vacuum source and/or a power source. The vacuum port may also include a hydrophobic membrane. The vent assembly may be recessed relative to the base or cover. The system may further include a divider having a plurality of longitudinal grooves formed on an underside thereof. The divider may further include a channel fluidly communicating the plurality of longitudinal grooves with at least one of the fluid inlet port and the vacuum port. The control unit may be directly connected to the vent assembly.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
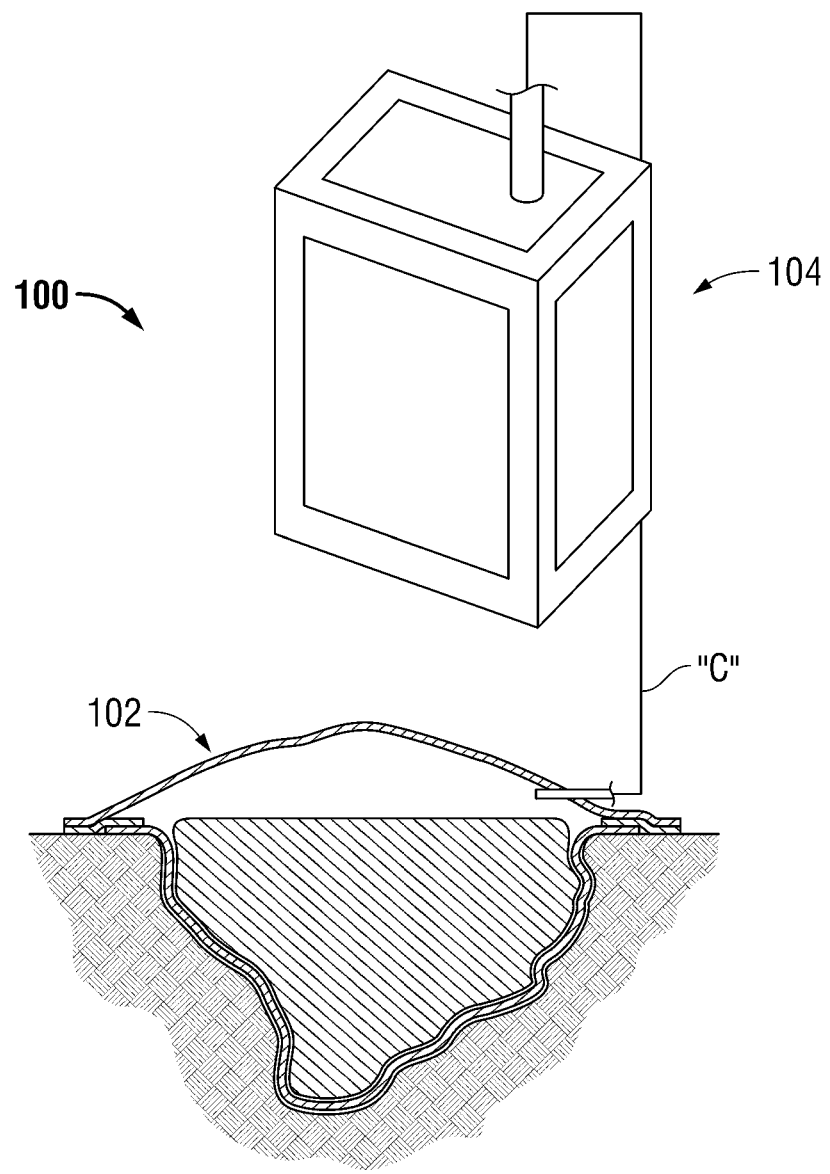
FIG. 1 is a view of a wound therapy system in accordance with the principles of the present disclosure.

The following figures illustrate embodiments of the present disclosure and are referenced to describe the embodiments depicted therein. Hereinafter, the disclosure will be described by explaining the figures wherein like reference numerals represent like parts throughout the several views.

Referring initially to FIG. 1, a wound therapy system of the present disclosure is shown generally as wound therapy system 100. Wound therapy system 100 includes composite wound dressing 102 and subatmospheric pressure mechanism 104 in fluid communication with the wound dressing 102 through a conduit, identified schematically as reference character "c". For a more detailed description of wound dressing 102, including the composition and operation thereof, please refer to commonly owned U.S. patent application Ser. No. 12/047,910, filed Mar. 13, 2008, the contents of which are incorporated herein by reference in their entirety.

Figure 2:
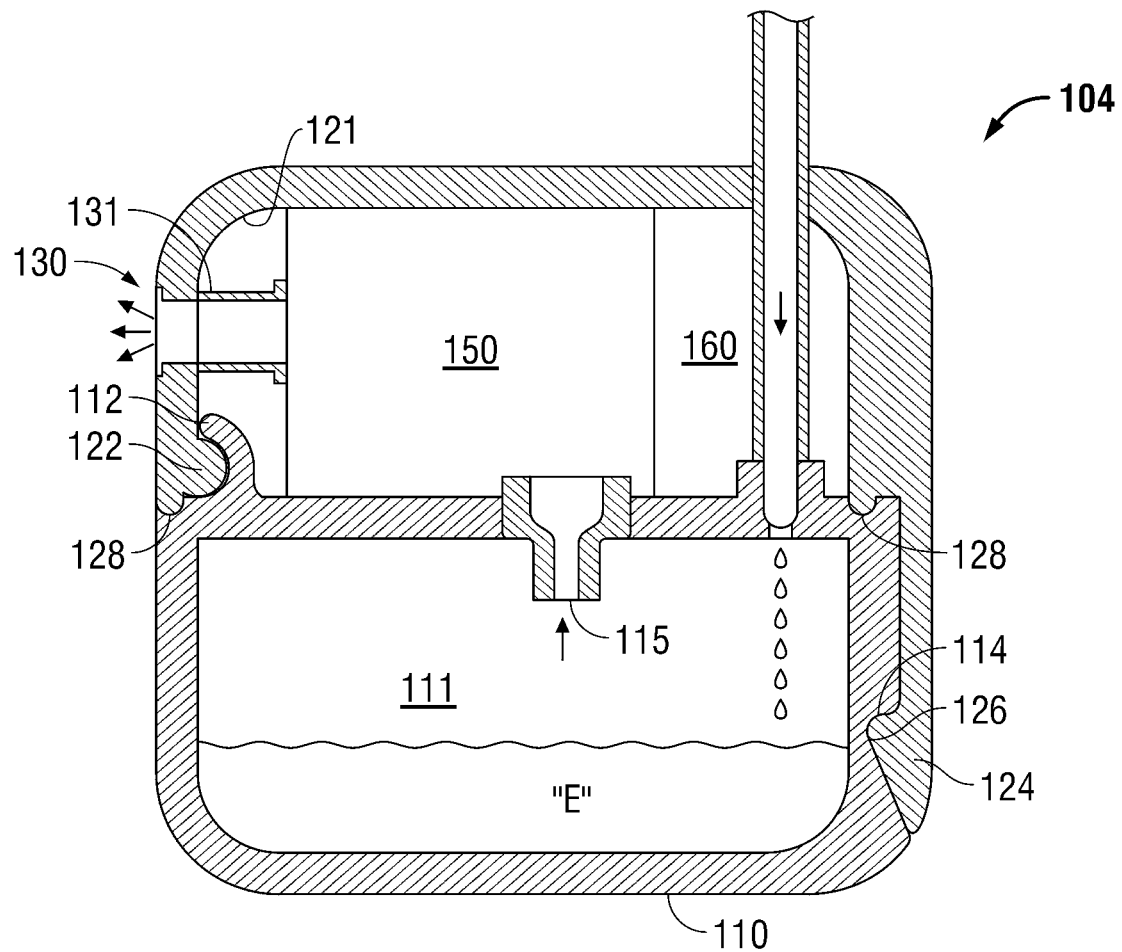
FIG. 2 is a side cross-sectional view of the subatmospheric pressure mechanism of the wound therapy system of FIG. 1.
Figure 3:
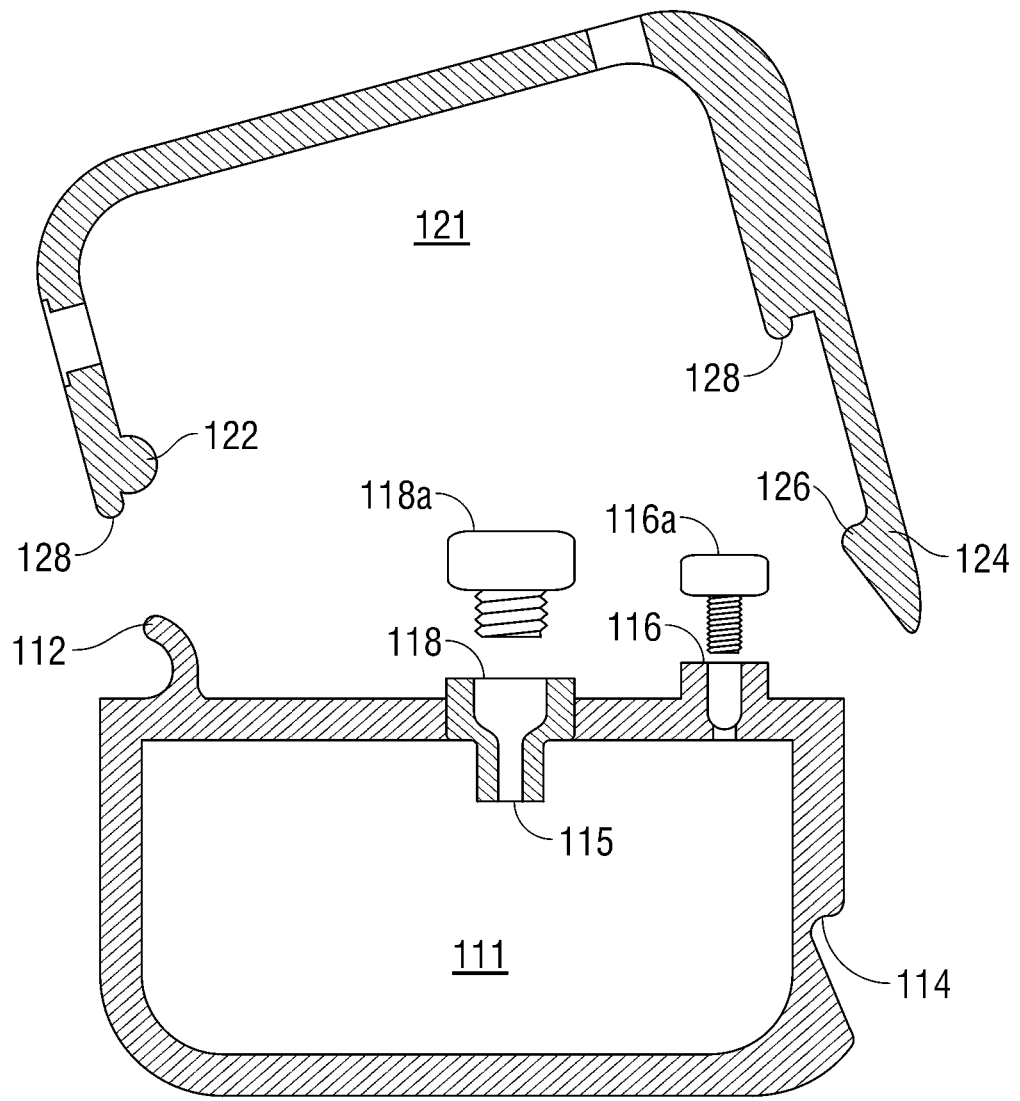
FIG. 3 is a side cross-sectional side view of the subatmospheric pressure mechanism of FIG. 2, illustrating the housing cover separated from the housing base.

With reference now to FIGS. 2-3, subatmospheric pressure mechanism 104 will be described in detail. Subatmospheric pressure mechanism 104 may be a portable canister adapted to be worn or carried by the subject via a strap, belt, or the like. In the alternative, pressure mechanism 104 may be a component of a non-ambulatory system. Subatmospheric pressure mechanism 104 includes housing base 110 and housing cover 120 selectively attachable to housing base 110. Housing base 110 and/or housing cover 120 may be fabricated from substantially rigid material, or in the alternative, include a relatively flexible material. Housing base 110 defines a first cavity 111 for receiving fluid, e.g. exudates "E" from wound dressing 102 (FIG. 1). Housing cover 120 defines a second cavity 121 to accommodate, e.g., a control unit for controlling operation of system 100. The control unit may consist of vacuum source 150, power source 160, and logic software and/or processing means for controlling operation of vacuum source 150 based on various parameters and/or in connection with a treatment regimen.

Housing base 110 and housing cover 120 may be adapted for releasable coupling. In one embodiment, housing base 110 includes flange 112 and notch or recess 114. Flange 112 is configured to engage lip 122 formed in housing cover 120. Notch 114 is configured to selectively receive a tab 126 of an extension 124 of housing cover 120. Housing base 110 further includes a fluid inlet 116 and a suction port 118. Fluid inlet 116 is configured to operably engage conduit "c" and may include a luer lock 112a. Inlet 116 is preferably configured to receive cap 116a for preventing leakage of exudates "E" and odor from first cavity 111 when housing cover 120 is separated from housing base 110. Suction port 118 is configured to operably engage vacuum source 150. Suction port 118 may include a hydrophobic membrane or filter 115 for preventing exudates "E" from being aspirated into vacuum source 150. Suction port 118 may also be configured to receive cap 118a to prevent fluid leakage during disposal of housing base 110.

With reference still to FIGS. 2 and 3, housing cover 120 is configured for releasable engagement with housing base 110 and includes second cavity 121 for receiving vacuum source 150 and power source 160. Vacuum source 150 and/or power source 160 may be maintained with housing cover 120 with rubber mounts (not shown) for reducing vibration within housing cover 120. Housing cover 120 may be constructed of and/or include STYROFOAM® or other sound dampening material. Housing cover 120 may include an overlay, having lights and/or buttons (not shown) for monitoring and controlling the operation of subatmospheric pressure mechanism 104. Housing cover 120 includes lip 122 configured to engage flange 112 of housing base 110. An extension 124 extends from housing cover 120 opposite lip 122 and is configured for operable engagement by a user. Extension 124 includes tab 126 configured to engage notch 114 formed in housing base 110. Extension 124 is configured to flex such that tab 126 may be selectively received within notch 114, thereby, releasably securing housing cover 120 to housing base 110. This snap-fit configuration may produce an audible sound when tab 126 is received within notch 114, thereby, notifying the user that housing cover 120 and housing base 110 are securely joined together.

Seal member 128 extends about housing cover 120 to form a seal between housing cover 120 and housing base 110 when housing cover 120 is selectively secured to housing base 110. Seal member 128 may be secured to housing cover 120 in any manner, including mechanical fastening, welding, and adhesive. Alternatively, seal member 128 may extend about housing base 110 to form a seal between housing base 110 and housing cover 120. In an alternative embodiment, seal member 128 may include two or more seal elements (not shown). Seal member 128 establishes and maintains a sealed relationship between cover 120 and housing base 110 when the components are assembled thereby preserving the integrity of the second cavity 121 within cover 120.

Figure 4A:
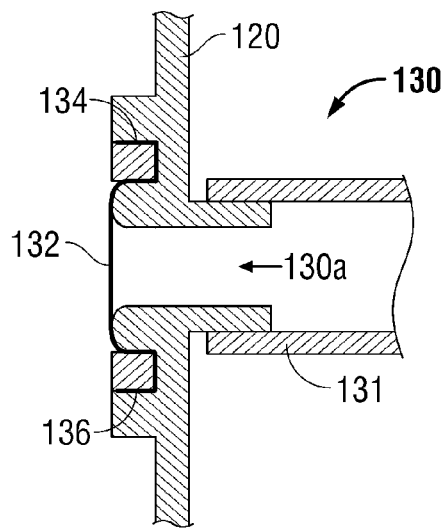
FIG. 4A is an enlarged side cross-sectional view of the vent assembly of the subatmospheric pressure mechanism of FIGS. 2 and 3.
Figure 4B:
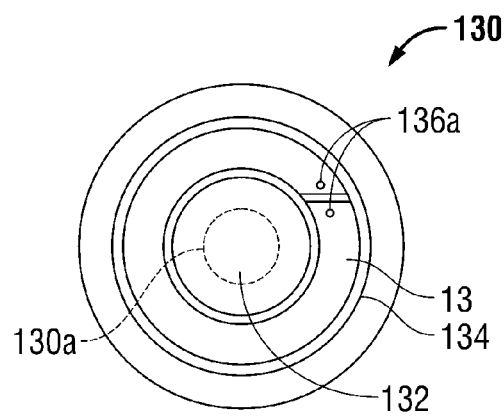
FIG. 4B is an enlarged plan view of the vent assembly of FIG. 4A.

Housing cover 120 further includes vent assembly 130 configured to vent exhaust air from vacuum source 150 through exhaust port 130a. Turning initially to FIGS. 4A and 4B, vent assembly 130 extends from housing cover 120 and is directly connected to vacuum source 150 (FIG. 1) via tube 131. Vent assembly 130 includes filter 132 extending across exhaust port 130a and split ring 136 for retaining filter 132 over exhaust port 130a. Vent assembly 130 includes groove 134 formed about exhaust port 130a adapted to receive split ring 136. Filter 132 is sized and dimension such that an outer portion of filter 132 folds into groove 134 and is retained therein by split ring 136. Filter 132 may be hydrophobic in nature and/or may include charcoal or other odor absorbing material, and may prevent the passage of bacteria. Split ring 136 may be formed of plastic, metal or other suitable material. Split ring 136 may include openings 136a configured to receive a tool for removing split ring 136 from within groove 134. In this manner, filter 132 may be changed as necessary.

Figure 5A:
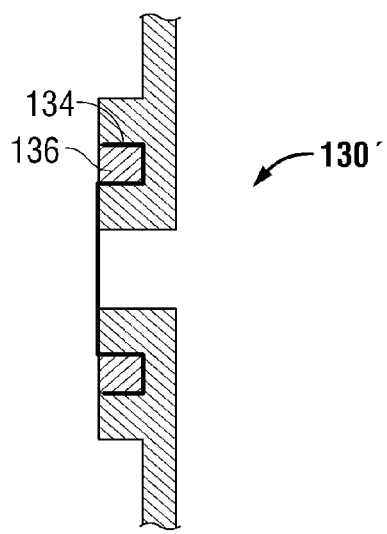
FIG. 5A is an enlarged side cross-sectional view of an alternate embodiment of the vent assembly of the subatmospheric pressure mechanism of FIGS. 2 and 3.
Figure 5B:
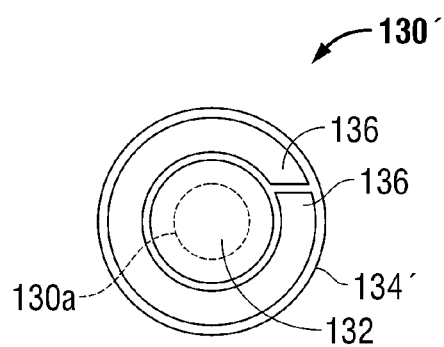
FIG. 5B is an enlarged front view of the vent assembly of FIG. 5A.

Turning now to FIGS. 5A and 5B, in an alternative embodiment, vent assembly 130' may be recessed in housing cover 120. Additionally, vent assembly 130' may vent exhaust air from within second cavity 121 rather than directly from vacuum source 150 via tube 131. In this manner, heat may be dissipated from within second cavity 121 in addition to the venting of exhaust from vacuum source 150. This configuration also provides a positive pressure on filter 132. Filter 132 is again retained within a groove 134' formed in housing 120 by split ring 136.

In operation, subatmospheric pressure mechanism 104 is adapted to draw exudates from wound dressing 102 via conduit "c". Initially, housing cover 120 is selectively secured to housing base 110. To secure housing cover 120 to housing base 110, lip 122 of housing cover 120 is first received within flange 112 of housing base 110. Housing cover 120 is then pivoted about flange 112 such that extension 124 received over housing base 110. Housing cover 120 is pivoted until tab 126 of extension 124 is received within notch 114. Subatmospheric pressure mechanism 104 may be configured such that receipt of tab 126 within notch 114 causes an audible sound, thereby confirming to a user that housing cover 120 has been securely received on housing base 110. Once subatmospheric pressure mechanism 104 is assembled, conduit "c" may be fluidly coupled to fluid inlet 116 and the control unit (not shown) may be activated. Activation of vacuum source 150 creates suction within first cavity 111 that draws exudates from wound dressing 102 through conduit "c". Exudates "E" collect in first cavity 111 of housing base 110. Exhaust from vacuum source 150 is vented either directly or indirectly through vent assembly 130, 130', respectively. Heat may also be dissipated through vent assembly 130'.

Upon filling of first cavity 111, completion of treatment or other any other reason, subatmospheric pressure mechanism 104 may be deactivated and exudates "E" may be properly disposed. To disengage housing cover 120 from housing base 110, extension 124 of housing cover 120 is flexed away from housing base 110. In this manner, tab 126 on extension 124 is withdrawn from engagement with notch 114 formed in housing base 120. Housing cover 120 may be pivoted away from housing base 110 until lip 122 of housing cover 120 disengages flange 112 of housing base 110. Once housing cover 120 is separated from housing base 110, exudates "E" may be disposed. Exudates "E" may be emptied from first cavity 111, or alternatively, housing base 110 may be disposed of in its entirety. In the event housing base 110 is disposed, caps 116a, 118a may be placed in fluid inlet 116 and suction port 118, respectively, such that housing base 110 may be transported without worry of fluid leakage or odor escaping from within cavity 111.

Figure 6:
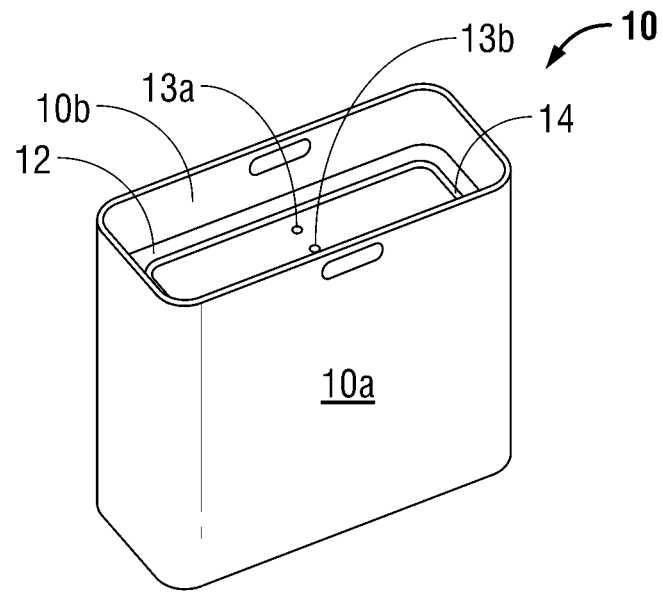
FIG. 6 is a perspective view of another subatmospheric pressure mechanism of the present disclosure.

With reference now to FIG. 6, a housing base of alternate embodiment of a subatmospheric pressure mechanism is shown as housing base 10. Housing base 10 includes divider 12 for separating housing base 10 into a fluid receiving portion 10a and an operational portion 10b configured for receiving a control unit, including a vacuum source and power source (not shown). Divider 12 includes a fluid inlet port 13a and a vacuum port 13b. Divider 12 further includes a gasket 14 extending about an outer periphery of divider 12. Gasket 14 is configured to engage vacuum source (FIG. 2) in a sealed manner, thereby enabling a vacuum to be created within fluid receiving portion 10a to draw fluid from wound dressing 102 (FIG. 1).

Figure 7:
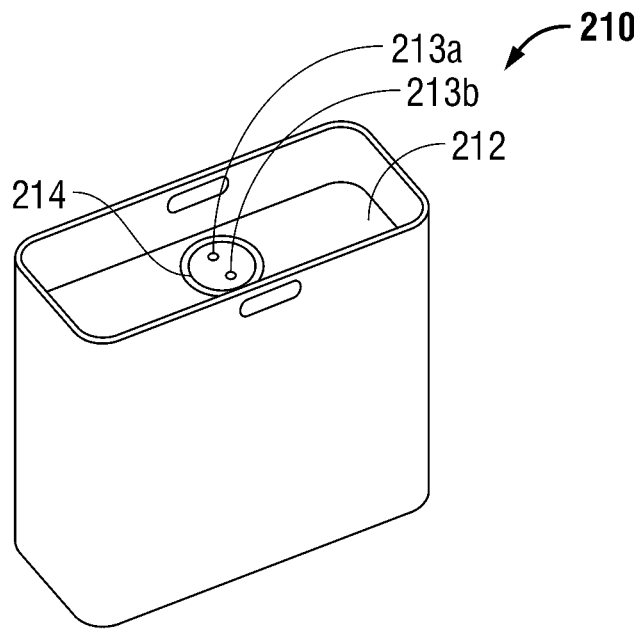
FIG. 7 is a perspective view of another embodiment of the subatmospheric pressure mechanism.

Turning now to FIG. 7, a housing base of an alternative embodiment of the subatmospheric pressure mechanism of the present disclosure is shown generally as housing base 210. Subatmospheric pressure mechanism 210 includes a divider 212 including a fluid inlet port 213a and vacuum port 213b. Divider 212 further includes a gasket 214 extending about fluid inlet port 213a and vacuum port 213b for engaging a vacuum source (FIG. 2) in a sealed manner. By localizing gasket 214 around fluid inlet port 213a and vacuum port 213b the likelihood of sealing issues, such as air and fluid leaks, is reduced. Gasket 214 may be formed of gel or other suitable sealing material. One preferred gel material is a silica gel.

Figure 8:
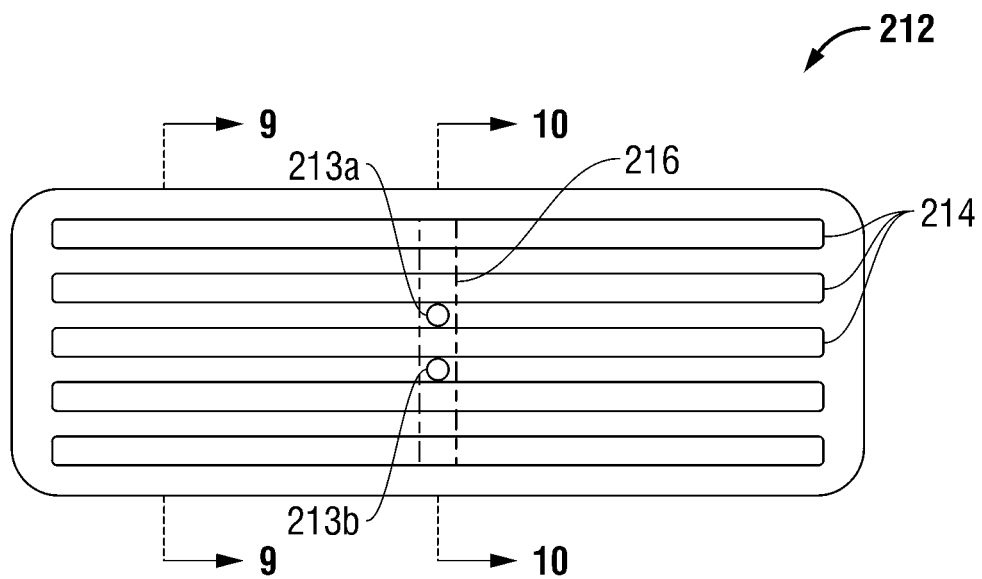
FIG. 8 is a plan view of the divider of the subatmospheric pressure mechanism of FIG. 7.
Figure 9:
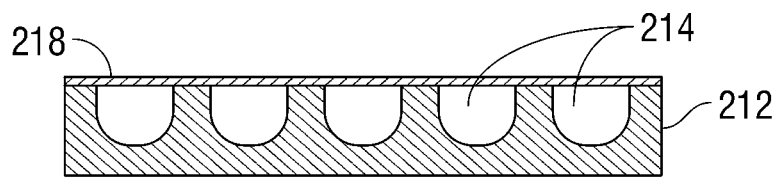
FIG. 9 is cross-sectional end view of the divider of FIG. 8 taken along line 9-9.
Figure 10:
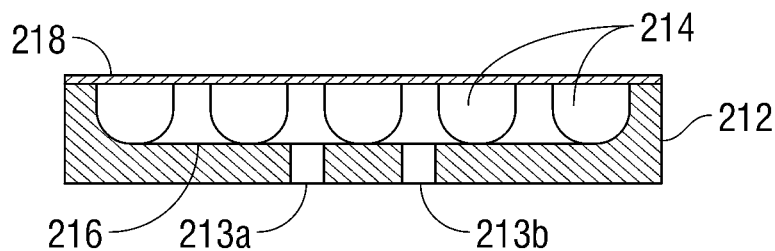
FIG. 10 is a cross-sectional view of the divider of FIG. 8 taken along line 10-10.

With reference now to FIGS. 8-10, underside 212a of divider 212 is configured to assist in fluid collection. Divider 212 includes a plurality of longitudinal grooves 214 extending the length thereof. Channel 216 extends the width of divider 212 in alignment with fluid inlet port 213a and vacuum port 213b. Channel 216 fluidly communicates each of the plurality of longitudinal grooves 214 with fluid inlet port 213a and vacuum port 213b. Divider 212 may be integrally formed with housing base 210, or as shown configured to be received within housing base 210. In this manner, divider 212 is sealed within housing base 210 using a hydrophobic adhesive or other suitable bonding material (not shown). Divider 212 may further include a hydrophobic membrane 218 at least partially covering longitudinal grooves and vacuum port 213b. Hydrophobic membrane 216 provides a fluid barrier between the fluid collection chamber and the control mechanism. Longitudinal grooves 214 provide increased surface area for air flow through hydrophobic membrane 218. This may assist vacuum flow, e.g., in the event that a portion of the surface area becomes clogged and/or covered with exudate "E" or other fluid.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A system for removing body fluid from body tissue, comprising:
   a conduit adapted to be in fluid communication with body fluid;
   a canister including,
      a base segment having a fluid receiving cavity in fluid communication with the conduit;
      a cover segment coupled to the base segment, the cover segment including a subatmospheric pressure source fluidly coupled to the fluid receiving cavity; and
      a divider segment disposed between the base segment and the cover segment, the divider segment including at least one groove in fluid communication with the fluid receiving cavity.

2. The system as in claim 1, wherein the divider segment includes a vacuum port fluidly coupling the subatmospheric pressure source with the fluid receiving cavity through the at least one groove.

3. The system as in claim 2, wherein the divider segment further comprises a hydrophobic membrane disposed on the divider segment, the hydrophobic membrane at least partially covering the vacuum port and the at least one groove.

4. The system as in claim 3, wherein the divider segment includes a plurality of grooves facing the fluid receiving cavity, each of the plurality of grooves in fluid communication with the fluid receiving cavity and the subatmospheric pressure source.

5. The system as in claim 4, wherein each of the plurality of grooves extends along a longitudinal axis of the divider segment.

6. The system as in claim 4, wherein the divider segment further includes a channel in fluid communication with each of the plurality of grooves.

7. The system as in claim 6, further comprising a means for coupling the base segment to the cover segment.

8. The system as in claim 1, further comprising a wound dressing fluidly connected to the conduit.

9. A subatmospheric pressure system for wound therapy, comprising:
   a cover segment including a subatmospheric pressure source;
   a base coupled to the cover segment, the base including a fluid receiving cavity;
   a divider disposed between the base and the cover, the divider including a vacuum port in fluid communication with the fluid receiving cavity and fluidly coupled to the subatmospheric pressure source, the divider further including a groove defined on a surface of the divider facing the fluid receiving cavity, the groove in fluid communication with the vacuum port; and
   a filter mounted on the divider, between the subatmospheric pressure source and the fluid receiving cavity.

10. The system as in claim 9, wherein the filter comprises a hydrophobic membrane.

11. The system as in claim 10, wherein the divider further comprises a channel defined on the surface, and wherein the divider comprises a plurality of grooves each defined on the surface, each of the plurality of grooves in fluid communication with the vacuum port through the channel.

12. The system as in claim 9, further comprising a wound dressing dimensioned for positioning relative to a wound bed of a subject.

13. A method of facilitating subatmospheric pressure therapy, comprising:
providing a portable system having a cover segment, a base segment coupled to the cover segment, and a divider disposed between the base segment and the cover segment, the cover segment including a subatmospheric pressure source, the base segment including a fluid receiving cavity fluidly coupled to the subatmospheric pressure source, the divider including a vacuum port, a groove defined on a surface of the divider facing the fluid receiving cavity, and a filter mounted on the divider between the subatmospheric pressure source and the fluid receiving cavity, the vacuum port fluidly coupling the subatmospheric pressure source and the fluid receiving cavity, the groove in fluid communication with the vacuum port and the fluid receiving cavity.

14. The method as in claim 12, further comprising providing a wound dressing fluidly connectable to the fluid receiving cavity.

15. The method as in claim 14, further comprising providing a cap fluidly isolating the fluid receiving cavity from the wound dressing.

16. The method as in claim 12, wherein the filter comprises a hydrophobic membrane.

17. The method as in claim 16, wherein the divider further comprises a channel defined on the surface, and wherein the divider comprises a plurality of grooves each defined on the surface, each of the plurality of grooves in fluid communication with the vacuum port through the channel.

18. The method as in claim 17, further comprising providing a plug configured to fluidly isolate the fluid cavity.

19. The method as in claim 17, wherein the divider further includes a seal disposed between the cover segment and the base.

20. The method as in claim 9, wherein the cover segment further comprises a power source coupled to the subatmospheric pressure source.

\* \* \* \* \*